US009261514B2

United States Patent
Kim et al.

(10) Patent No.: US 9,261,514 B2
(45) Date of Patent: Feb. 16, 2016

(54) CONFORMATIONAL-SWITCHING FLUORESCENT PROTEIN PROBE FOR DETECTION OF ALPHA SYNUCLEIN OLIGOMERS

(71) Applicant: New York University, Brooklyn, NY (US)

(72) Inventors: Jin Ryoun Kim, Jericho, NY (US); Michael Hernandez, Ozoner Park, NY (US)

(73) Assignee: New York University, Brooklyn, NY (US)

( * ) Notice: Subject to any disclaimer, the term of this patent is extended or adjusted under 35 U.S.C. 154(b) by 0 days.

(21) Appl. No.: 14/330,445

(22) Filed: Jul. 14, 2014

(65) Prior Publication Data

US 2015/0017739 A1  Jan. 15, 2015

Related U.S. Application Data

(60) Provisional application No. 61/846,246, filed on Jul. 15, 2013.

(51) Int. Cl.
*G01N 33/542* (2006.01)
*C07K 14/47* (2006.01)
*G01N 33/68* (2006.01)

(52) U.S. Cl.
CPC ............ *G01N 33/6896* (2013.01); *C07K 14/47* (2013.01); *G01N 33/542* (2013.01); *G01N 2800/2835* (2013.01)

(58) Field of Classification Search
None
See application file for complete search history.

(56) References Cited

U.S. PATENT DOCUMENTS

2002/0037908 A1 * 3/2002 Douglas et al. ............... 514/350

OTHER PUBLICATIONS

Cremades 2012 "Direct observation of the interconversion of normal and toxic forms of .alpha.-synuclein" Cell 149:1048-1059.*
Nakamura 2008 "Optical reporters for the conformation of .alpha.-synuclein reveal a specific interaction with mitochondria" J Neurosci 28(47):12305-12317.*
Roberti 2007 "Fluorescence imaging of amyloid formation in living cells by a functional, tetracysteine-tagged .alpha.-synuclein" Nature Methods 4(4):345-351.*

* cited by examiner

*Primary Examiner* — Gregory S Emch
*Assistant Examiner* — Adam M Weidner
(74) *Attorney, Agent, or Firm* — Laurence P. Colton; Smith Risley Tempel Santos LLC

(57) ABSTRACT

A conformation-switching fluorescent protein probe for detection of alpha synuclein oligomers using an alpha synuclein (αS) variant, PG65 (SEQ ID NO: 4), together with a conformation-sensitive fluorescent molecule to create a molecular probe for rapid, specific, and quantitative detection of αS oligomers.

12 Claims, 11 Drawing Sheets

| | N-terminus | HNAC | tetra-cysteine | HNAC | linker | HNAC | C-terminus |
|---|---|---|---|---|---|---|---|
| PG65 | M1-K60 | E61-T64 | CCPGCC | A69-V82 | E83-G86 | S87-V95 | K96-A140 |

| | N-terminus | HNAC | tetra-cysteine | HNAC | linker | HNAC | C-terminus |
|---|---|---|---|---|---|---|---|
| PG65F | M1-K60 | E61-T64 | HRW CCPGCC KTF | A69-V82 | E83-G86 | S87-V95 | K96-A140 |

| | N-terminus | HNAC | linker | HNAC | tetra-cysteine | HNAC | C-terminus |
|---|---|---|---|---|---|---|---|
| PG83 | M1-K60 | E61-T64 | N65-G68 | A69-V82 | CCPGCC | S87-V95 | K96-A140 |

| | N-terminus | HNAC | linker | HNAC | tetra-cysteine | HNAC | C-terminus |
|---|---|---|---|---|---|---|---|
| PG83F | M1-K60 | E61-T64 | N65-G68 | A69-V82 | HRW CCPGCC KTF | S87-V95 | K96-A140 |

FIG. 5

CONFORMATIONAL-SWITCHING FLUORESCENT PROTEIN PROBE FOR DETECTION OF ALPHA SYNUCLEIN OLIGOMERS

STATEMENT OF RELATED APPLICATIONS

This patent application is the non-provisional of and claims priority to U.S. Provisional Patent Application No. 61/846,246 having a filing date of 15 Jul. 2013.

SEQUENCE LISTING

The instant application contains a Sequence Listing which has been submitted electronically in ASCII format and is hereby incorporated by reference in its entirety. Said ASCII copy, created on Sep. 26, 2014, is named 48467.056U1_SL.txt and is 3,689 bytes in size.

BACKGROUND OF THE INVENTION

1. Technical Field

The present invention is generally related to the use of intrinsically disordered proteins as conformation-switching biosensors, and more specifically related to the use of an alpha synuclein (αS) variant, PG65, together with conformation-sensitive fluorescence to create a molecular probe for rapid, specific and quantitative detection of αS oligomers, which are the major toxic aggregate forms in Parkinson's disease.

2. Prior Art

Aggregation of a synuclein (αS), which is a 140-amino acid, structurally flexible, intrinsically disordered protein (IDP), is central to the pathogenesis of Parkinson's disease (PD).[1] αS aggregation involves a molecular process of monomeric αS self-assembling to form αS oligomeric forms followed by further stacking into large fibrillar αS aggregates[2]. The distinct αS aggregate assemblies display different, yet similar, conformations and exert a varying extent of biological effects.[3] Despite its scientific and biomedical importance, the exact nature of αS aggregation is poorly understood, in part due to the limited capability to detect structurally similar yet different αS assemblies specifically and reliably.[4]

The non-β amyloid component domain (E61-V95, NAC) of αS is critical in αS self-assembly.[5] Within the NAC domain, hydrophobic residues with high β sheet potentials (referred to as HNAC in FIG. 1A) are connected by residues with high turn potentials (referred to as the linker region in FIG. 1A).[6] αS monomers are irregularly structured.[1] αS oligomers are soluble aggregates which may possess β sheet structures.[7] αS oligomers may display different structures depending on size (e.g., low molecular weight (LMW) vs. high molecular weight (HMW) αS oligomers).[7a] A structural variation can also exist between HMW αS oligomers formed under different incubation conditions.[7b] αS oligomers can further aggregate to αS fibrils exhibiting cross β sheet structures[8] which are similar, but not necessarily identical to β sheet conformations found in αS oligomers.[7b,9] In particular, arrangements of β strands in β sheets differ between oligomers and fibrils of αS[7b], as is the case with other amyloid proteins.[10]

It is widely accepted that β sheet-structured αS oligomers are the major toxic agents in PD[7,11]. Neither early diagnostics nor disease-modifying drugs are currently available for PD, and specific detection of αS oligomers is quintessential to develop relevant strategies as well as to better understand a molecular basis of PD. A rapid-responsive rather than overnight-long platform is preferred for detection of αS oligomers due to their structurally transient nature.[7b,12] Such detection should also benefit high-throughput assays to identify therapeutic agents specifically inhibiting αS oligomerization rather than αS fibrillization. Note that compounds inhibiting αS fibrillization are not necessarily effective at inhibition of αS oligomerization[13] and incomplete prevention of αS fibrillization may result in an accumulation of αS oligomers. Quantitative detection of αS oligomers is essential for correct profiling of oligomeric states. Unfortunately, many, if not all, molecular probes responding to αS oligomers are also responsive to αS fibrils.[4] Indeed, rapid-responsive, quantitative, αS oligomer-specific detection methods are currently unavailable.

A known peptide probe for diagnostics and therapeutics is shown in European Patent Publication No. EP 2156181 A2 to Cindy S. Orser et al. A known method for the detection of conformationally altered proteins is shown in European Patent No. EP 1700096 B1 to Eugene Davidson et al. Known dyes for analysis of protein aggregation are shown in European Patent Publication No. EP 2507319 A2 to Anatoliy Balanda et al. Known methods, compositions, and kits for detecting protein aggregates are shown in European Patent No. EP 2019836 B1 to Karl J Guegler.

A known peptide probe for rapid and specific detection is shown in US Patent Publication No. US 20130017615 A1 to Jin Ryoun Kim et al. A known sensor device for determining protein aggregation is shown in European Patent Publication No. EP 1556704 A1 to David Allsop et al. Known methods of preventing, treating and diagnosing disorders of protein aggregation are shown in European Patent No. EP 1608350 B1 to Joanne Mclaurin. Known alpha synuclein aggregation assays are shown in European Patent Publication No. EP 1366368 A2 to Daniel Benjamin et al. A known protein stability assay using a fluorescent reporter of protein folding is shown in US Patent Publication No US 20110129935 A1 to Patrick Schaeffer.

Known compounds for use in the detection of neurodegenerative diseases are shown in US Patent Publication No. US 20120251448 A1 to Franz F. Hefti et al. Known antibodies to alpha synuclein are shown in US Patent Publication No. US 20130072663 A1 to Tamie J. Chilcote et al. A known probe for analyzing protein-protein interaction and method of analyzing protein-protein interactions with the use of the same is shown in European Patent No. EP 1229330 B1 to Takeaki Ozawa et al.

Accordingly, there is a need for a conformation-switching fluorescent protein probe for detection of alpha synuclein oligomers and to the use of an alpha synuclein (αS) variant, PG65, together with conformation-sensitive fluorescence to create a molecular probe for rapid, specific and quantitative detection of αS oligomers. It is to these needs and others that the present invention is directed.

BRIEF SUMMARY OF THE INVENTION

Briefly, the present invention is a novel design paradigm to engineer the structural flexibility of an IDP variant to create a conformation-switching protein probe, PG65, for rapid, specific and quantitative detection of αS oligomers. PG65 is an engineered variant of intrinsically disordered αS and can bind to αS. The present invention exploits the structural flexibility of PG65 and conformation-sensitive fluorescence in such a way that 1) binding of PG65 to αS is functionally linked to generation of fluorescence signals, and 2) such a linkage is further regulated depending on αS aggregation states.

The present invention demonstrates that 1) one can create a rapid-responsive, conformation-switching protein probe for quantitative detection of β sheet-structured αS oligomers by exploiting the structural flexibility of an αS variant and conformation-sensitive fluorescence, 2) a linkage between binding to analytes and signaling can be modulated by binding-induced conformational changes of the protein probe, and 3) this linkage offers rapid and selective detection of HMW αS oligomers. Overall, the present strategy to engineer the structural flexibility of IDP variants represents a new paradigm for designing molecular probes, and can be applied to other IDPs, if necessary, with incorporation of a binding site for target analytes.

These features, and other features and advantages of the present invention will become more apparent to those of ordinary skill in the relevant art when the following detailed description of the preferred embodiments is read in conjunction with the appended drawings in which like reference numerals represent like components throughout the several views.

BRIEF DESCRIPTION OF THE DRAWINGS

FIG. 1A show amino acid sequence schematics of αS (SEQ ID NO: 2) and PG65 (SEQ ID NO: 4). αS does not contain any cysteine residues. FIG. 1A discloses 'CCPGCC as SEQ. ID. NO: 1. FIG. 1B shows relative FlAsH fluorescence changes (RFC) of PG65 at 0.5 µM as a function of monomer-equivalent molar concentrations of αS monomers (red circles), αS oligomers (black squares) and αS fibrils (blue triangles). $K_d=1\pm0.1$ µM for detection of αS oligomers.

FIG. 5 shows amino acid sequence schematics of PG65, PG65F, PG83 and PG83F. The sequences of PG65 and PG83 are similar to that of αS, except for replacement of the first or second linker region, respectively, with CCPGCC (SEQ ID NO: 1). PG65F and PG83F are similar to PG65 and PG83, respectively, except for the addition of HRW and KTF residues flanking CCPGCC (SEQ ID NO: 1). Inclusion of additional flanking residues HRW and KTF to the ends of a tetracysteine motif was previously found to improve FlAsH fluorescence.[2] FIG. 5 discloses 'HRWCCPGCCKTF' as SEQ ID NO: 5.

In FIG. 6D, 1 µg of αS from αS monomer, αS oligomer, or αS fibril samples was dotted onto a nitrocellulose membrane and probed with A11 and N19. A11 recognizes specific conformational structures present in certain oligomers formed by various amyloidogenic proteins[6]. N19 is a sequence specific antibody recognizing the N-terminus of αS.[11] In FIG. 6F, insets represent 5× magnification, highlighting the morphological differences between αS species present in αS monomer and αS oligomer samples. The inset image of αS oligomer samples illustrates annular and donut-like morphology of αS aggregates. Scale bars represent 200 nm in larger images. Inset scale bars represent 20 nm.

In FIG. 7C, ThT fluorescence of αS fibril samples is included for comparison. Scale bars in FIG. 7E represent 200 nm. In FIG. 7B and FIG. 7C, the errors represent one standard deviation from measurements of at least three samples. In FIG. 7F, αS oligomer concentrations were 2.5 µM monomer-equivalent concentration and the errors were evaluated using the propagation of error method.

at different molar concentrations of αS in FIG. 9A αS monomer and FIG. 9B αS oligomer samples. PG65 and αS were labeled with fluorescent dyes, Alexa Fluor 647 and Alexa Fluor 488, respectively. Concentration of PG65: 3.4 μM (lanes 1, 3, 5, 7 and 8) and concentration of αS: 2.5 μM (lanes 2 and 3), 10 μM (lanes 4 and 5), 20 μM (lanes 6 and 7). PG65 at <3.4 μM was not used because of insufficient fluorescence emission for imaging. Additional bands of PG65 formed as a result of its binding to LMW and HMW αS oligomers are shown in the enclosed solid and dashed lines, respectively. M: monomeric state, LMWO: LMW αS oligomers and HMWO: HMW αS oligomers.

DETAILED DESCRIPTION OF PREFERRED EMBODIMENTS

Figure 1:
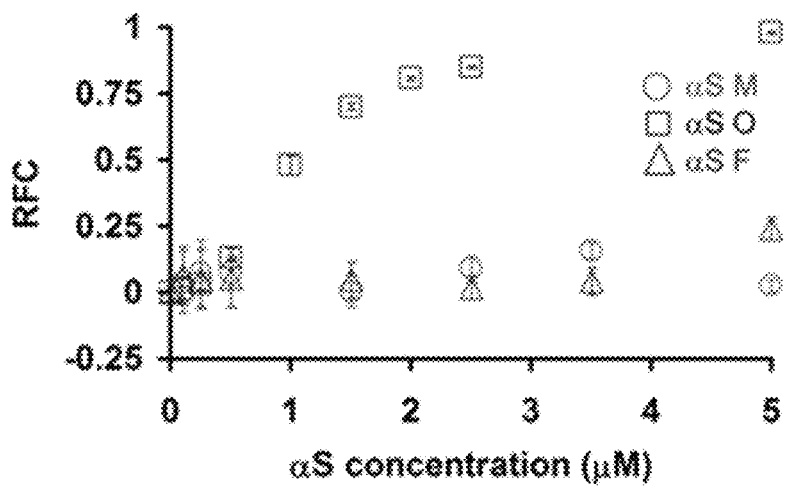

PG65 was created by replacement of the first αS linker region with a tetracysteine motif, CCPGCC (SEQ. ID NO: 1), as a binding site of a conformation-sensitive biarsenic fluorescent dye, FlAsH[14] (FIG. 1A). The αS can comprise the initial sequence of:

```
MDVFMKGLSKAKEGVVAAAEKTKQGVAEAAGKTKEGVLYVGSKTKEGV
VHGVATVAEKTKEQVTNVGGAWTGVTAVAQKTVEGAGSIAAATGFVKK
DQLGKNEEGAPQEGILEDMPVDPDNEAYEMPSEEGYQDYEPEA
(SEQ ID NO: 2),
``` and the PG65 useful in the present invention replaces the NVGG (SEQ ID NO: 3) with CCPGCC (SEQ ID NO: 1) resulting in a protein comprising the sequence:

```
MDVFMKGLSKAKEGVVAAAEKTKQGVAEAAGKTKEGVLYVGSKTKEGV
VHGVATVAEKTKEQVTCCPGCCAVVTGVTAVAQKTVEGAGSIAAATGF
VKKDQLGKNEEGAPQEGILEDMPVDPDNEAYEMPSEEGYQDYEPEA
(SEQ ID NO: 4).
```

Figure 3:
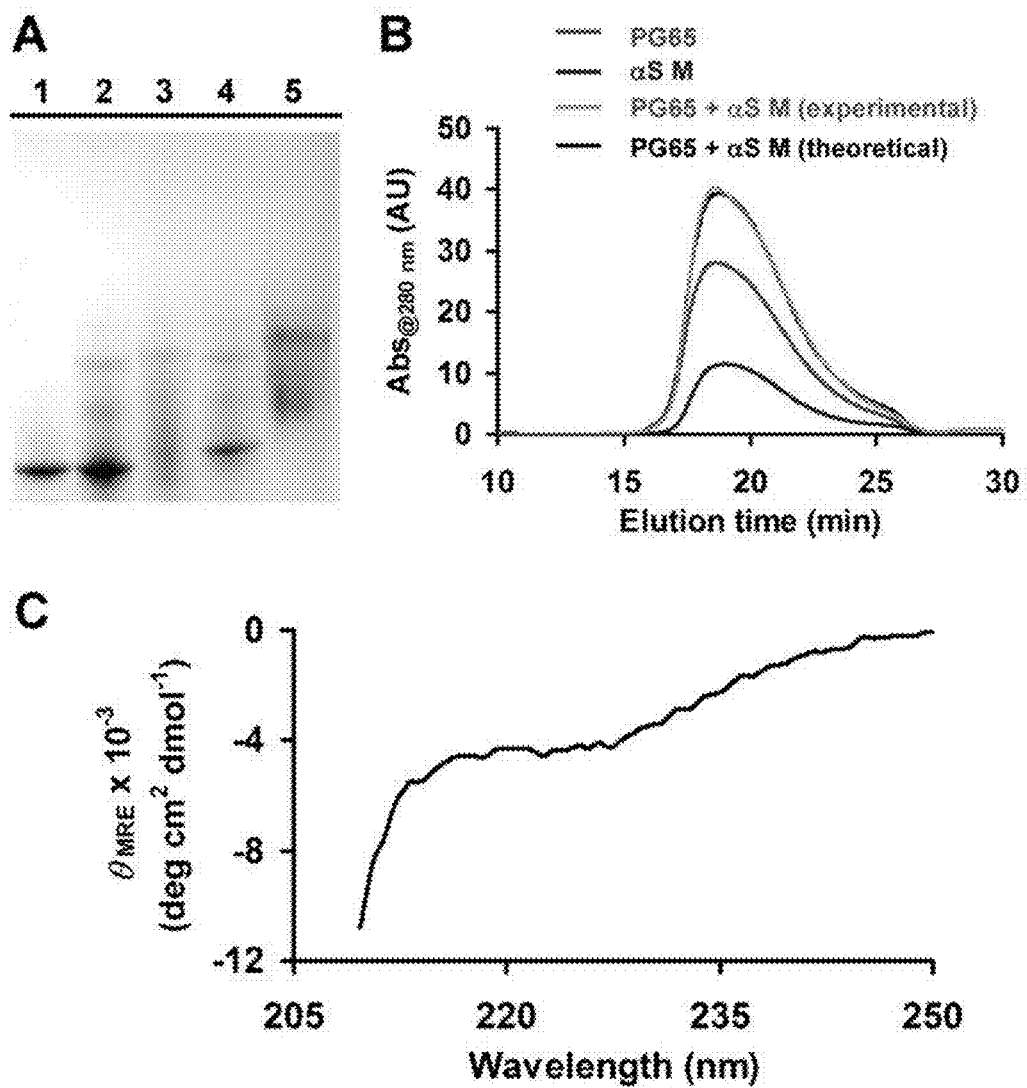
FIG. 3A shows native-PAGE of αS monomers (lane 1), PG65 (lane 2), PG65F (lane 3), PG83 (lane 4) and PG83F (lane 5) at 35 µM. PG65 existed as predominantly monomeric when compared to other protein probes including PG65F, PG83 and PG83F. Monomeric probes are preferred rather than oligomeric probes due to simplicity and ease of control.
FIG. 3B shows SEC spectra of PG65 at 35 µM (red line), αS monomer sample at 35 µM (blue line), a mixture of PG65+αS monomer sample at 35 µM each (green line) and a simple sum of individual spectra of PG65 and αS monomer sample (black line). PG65 remained mostly monomeric in aqueous buffer for >3 hours under this condition. Elution times of the major peaks were the same in all samples and the ratio of the major peak area of the mixture sample (i.e., PG65+αS monomers) to that of the simple sum of individual proteins was 1.01±0.03, indicating the lack of strong binding between PG65 and αS monomers. The void volume for the SEC column corresponded to 10 min under our experimental setup.
FIG. 3C shows a CD spectra illustrating the intrinsically disordered nature of PG65.
Figure 4:
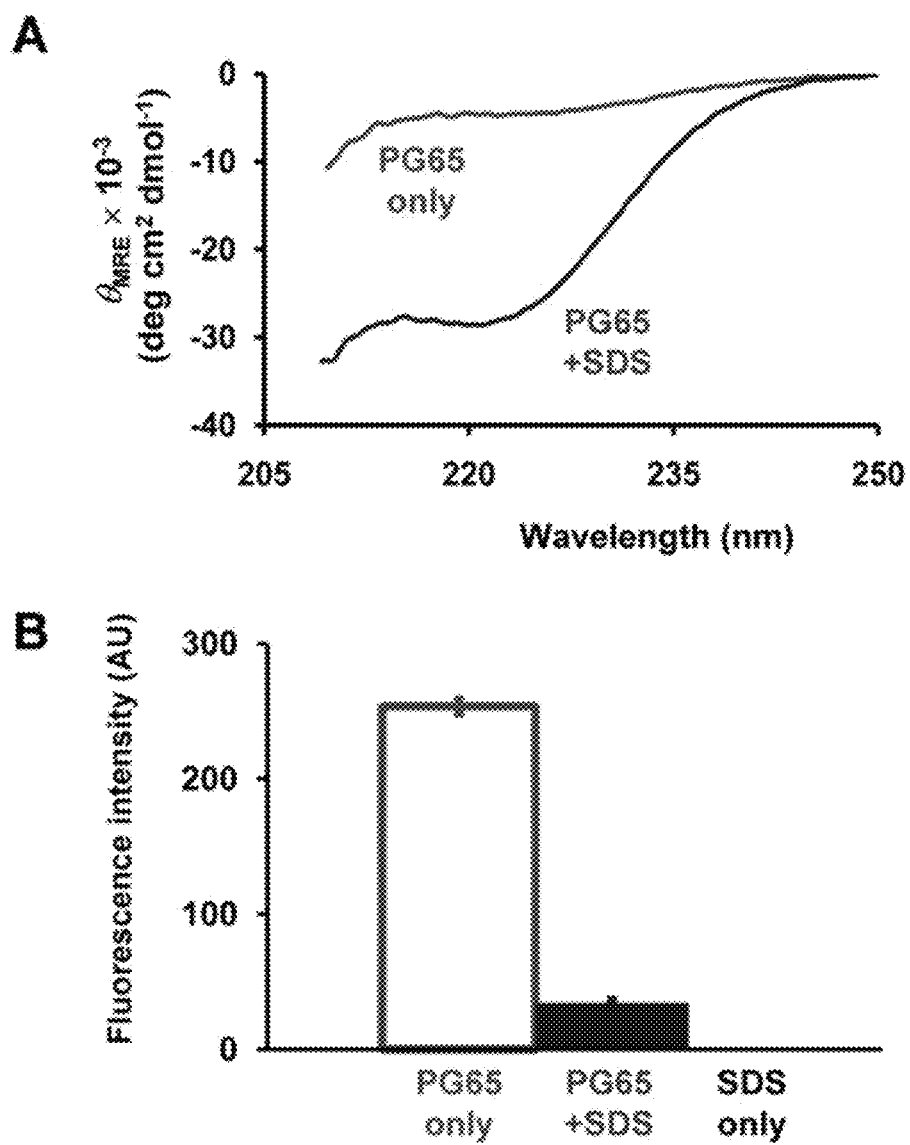
FIG. 4A shows a CD spectrum of PG65 in the presence (blue line) or absence (red line) of 0.75 mM SDS.
FIG. 4B shows FlAsH fluorescence of PG65 in the presence (blue filled bar) or absence (red empty bar) of 0.75 mM SDS. Results shown in FIG. 4A and FIG. 4B illustrate that PG65 was structurally flexible, displaying an SDS-dependent structure change similar to αS[1] and this structure change was mirrored by FlAsH fluorescence change. The implication is that PG65 generated FlAsH fluorescence signals in its conformation-dependent manner. There was no significant change in CD and FlAsH fluorescence signals of PG65 in the presence of 0.1 mM SDS when compared to a PG65 only control (data not shown).

FlAsH is non-fluorescent on its own, but becomes rapidly fluorescent upon binding to a tetracysteine motif through covalent arsenic-thiol binding.[14] PG65 can bind to αS presumably through the shared HNAC domains known to be critical in αS self-assembly.[5] Note that conformational changes of αS take place upon its self-assembly particularly at its HNAC domains around a linker region.[7b,8,15] As such, it is postulated that the present engineered αS variant (i.e., PG65) might display similar structural flexibility facilitating its conformational change upon binding to αS. Such a conformational change can then be linked to fluorescence signalling owing to strong dependence of FlAsH fluorescence on conformation in or around a tetracysteine motif.[14] It also is reasoned that conformational changes of PG65 might occur to different extents upon binding to structurally distinct, though similar, αS aggregates, as is the case with binding of other naturally existing IDPs to different ligands.[16] Different PG65 conformational states induced by binding to different αS aggregate species can further modulate resulting signals through high sensitivity of FlAsH fluorescence to conformational variation.[14,17] Altogether, it is envisioned that PG65 can could rapidly display fluorescence signals in response to specific αS aggregates by virtue of a dual mechanism involving binding and its coupling to signalling. Monomeric rather than oligomeric probes were preferred due to simplicity and ease of control. As desired, PG65 was mostly monomeric, structurally disordered under our experimental conditions (FIG. 3) and generated FlAsH fluorescence signals in its conformation-dependent manner (FIG. 4). Other protein probes were also created (FIG. 5) and found to be more aggregation-prone than PG65 (FIG. 3).

Figure 6:
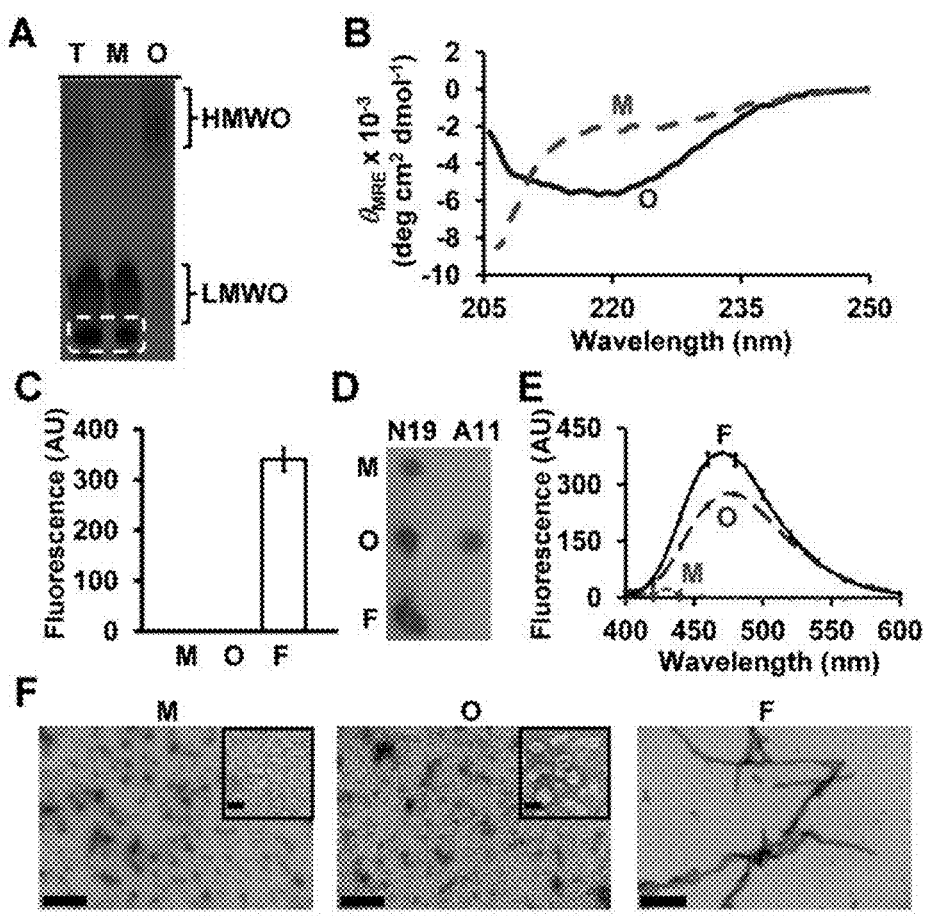
FIG. 6A shows native-PAGE of freshly prepared αS sample (T), αS monomer sample (M) and αS oligomer sample (O) containing HMW αS oligomer species (HMWO). To prepare αS monomer samples, freshly prepared αS samples were filtered using 100 kDa cutoff centrifugal filters followed by collection of filtrate. Retentate obtained from similar ultrafiltration of fresh αS samples after 6 hour incubation at 37° C. was collected to prepare αS oligomer samples. The bands corresponding to αS monomeric states are shown in the white enclosed dashed line. The presence of LMW αS oligomeric species (LMWO) in αS M and αS O samples was also detected and no further separation was attempted.
FIG. 6B shows a CD spectra of αS monomer (red dotted line) and αS oligomer samples (blue solid line).
FIG. 6C shows thioflavin T (ThT) fluorescence.
FIG. 6D shows A11 dot blot assays.
FIG. 6E shows ANS fluorescence.
FIG. 6F shows transmission electron microscopy (TEM) images of αS monomer (M), αS oligomer (O) and αS fibril (F) samples we prepared.

Freshly prepared PG65 at 0.5 μM was incubated for one hour with and without αS (see FIG. 6 for characterization of αS samples) followed by the addition of 1.5 μM FlAsH prior to fluorescence measurements. Importantly, PG65 generated significant relative fluorescence changes (RFCs) with αS oligomers, but not with αS monomers or αS fibrils (FIG. 1B). The αS oligomer-dependent RFC increased linearly with an increasing αS concentration ($R^2=0.95$) and then leveled off at ~2.5 μM of αS (FIG. 1B), suggesting that quantification of αS oligomers is achievable within this linear range. The observed FlAsH fluorescence signals originated from a change in quantum yield of FlAsH: the ratio of the FlAsH fluorescence change to the FlAsH quantum yield change of PG65 upon addition of αS oligomers was ~1, when measured as described previously.[18] PG65 effectively probed the presence of αS oligomers at ≥1.5 μM, an potentially at ≥1.0 μM, (FIG. 1B), an αS concentration close to physiological relevance.[19] This sensitivity corresponded to detection of ~3 μg of αS oligomers under our experimental setup, and potentially at ~2.0 μg or ~3.0 μg. Detection of αS oligomers using PG65 was not compromised by other αS forms: the ratio of RFCs of PG65 with a sample containing monomers, oligomers and fibrils of αS altogether at 2.5 μM each to a sample containing αS oligomers only at 2.5 μM was ~1.

Figure 2:
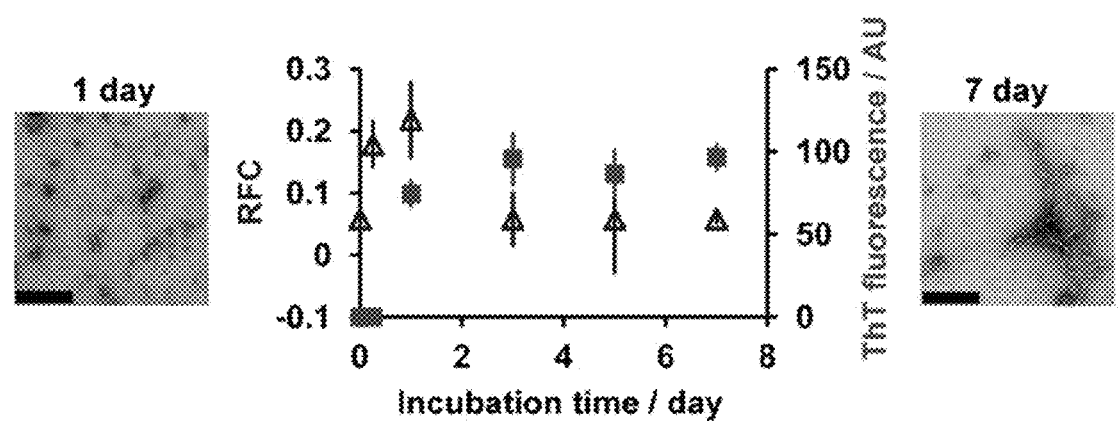
FIG. 2 shows time-course aggregation of αS in aqueous buffer monitored by FlAsH fluorescence of PG65 (empty blue triangles) and ThT fluorescence (filled red squares). Freshly prepared αS samples were incubated at 350 µM and 37° C. with constant shaking. Samples were then withdrawn during incubation at designated time points for examination of aggregation states. TEM images taken on αS samples after 1 and 7 day incubations are shown alongside. Scale bars: 200 nm.
Figure 7:
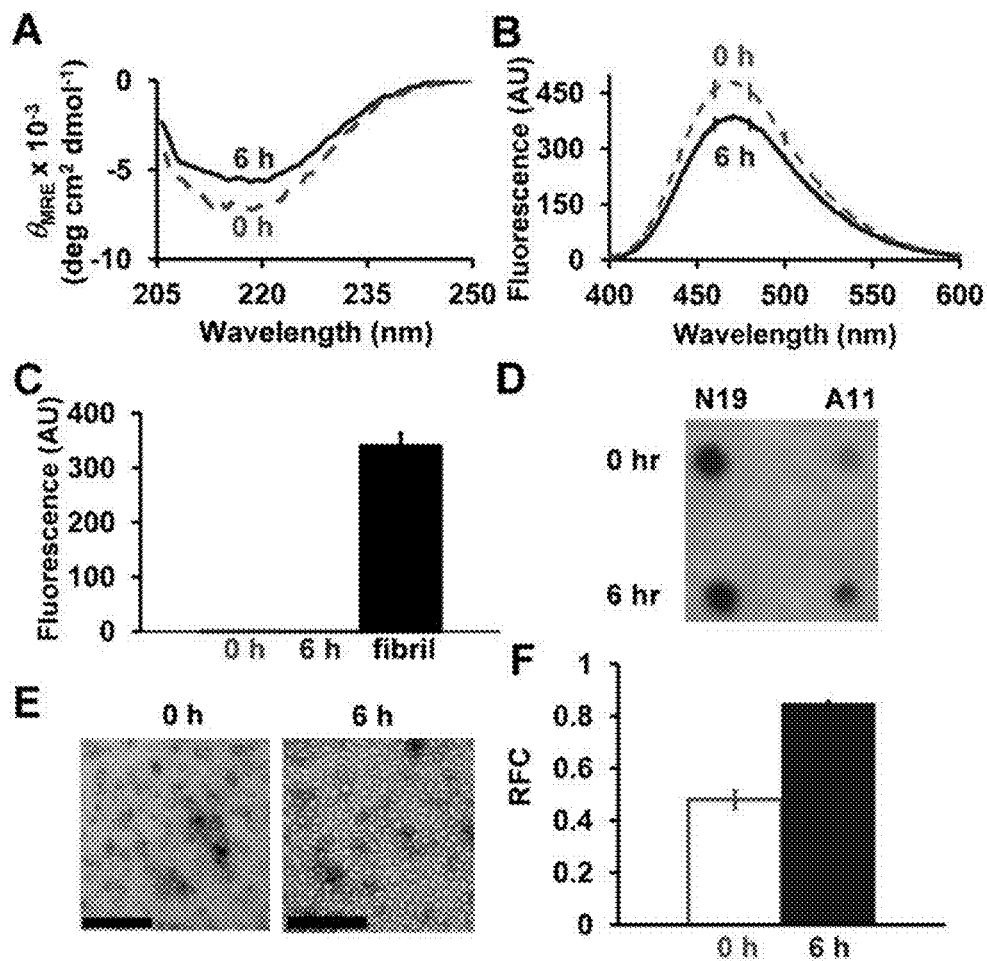
FIG. 7A shows a CD spectra.
FIG. 7B shows ANS fluorescence.
FIG. 7C shows ThT fluorescence.
FIG. 7D shows A11 dot blot with N19 loading control.
FIG. 7E shows TEM.
FIG. 7F shows RFC comparison between αS oligomer samples prepared after 0 h incubation (0 h) and 6 h incubation (6 h).
Figure 9:
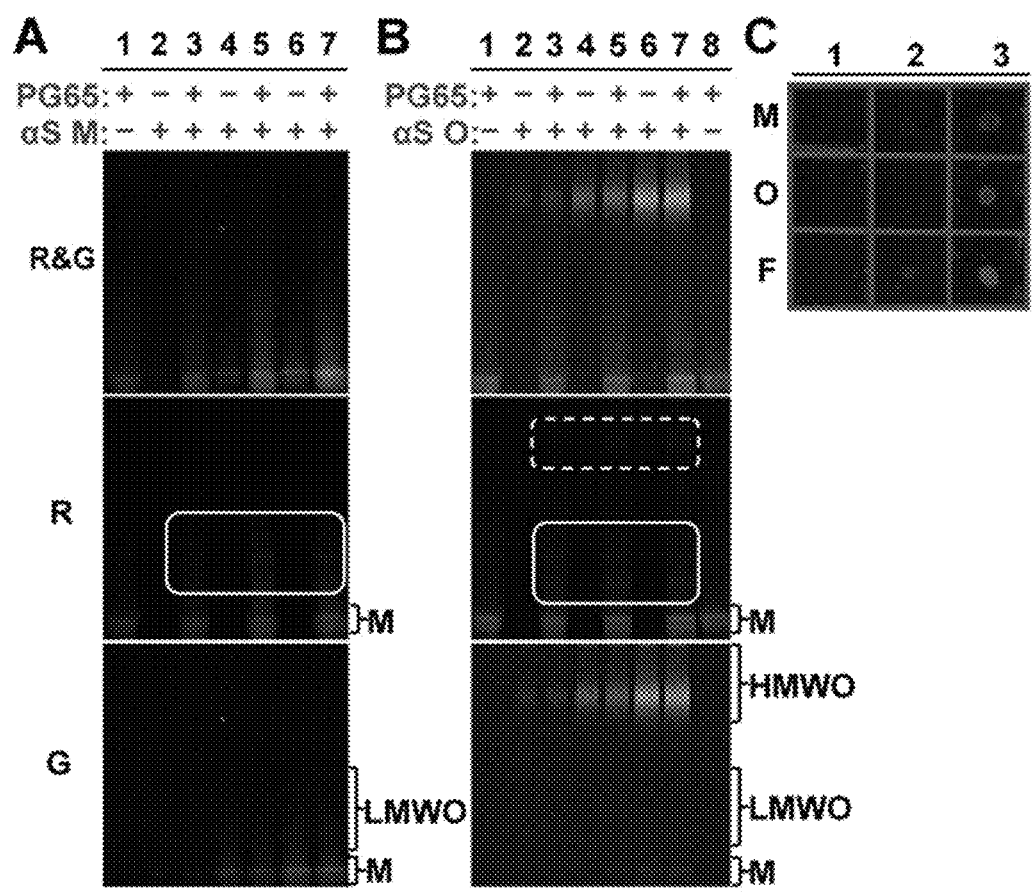
FIG. 9A and FIG. 9B show native-PAGE of PG65 (red, R), αS (green, G), and a mixture of PG65 (red, R)+αS (green, G)
FIG. 9C shows fluorescent dot blot assays of αS monomer (M), αS oligomer (O) and αS fibril (F) samples at 0.1 (column 1), 1 (column 2) and 10 μg (column 3) of αS probed with Alexa Fluor 647-labeled PG65 containing Cys to Ser mutations. No significant difference in electrophoretic patterns of protein samples was detected in the presence and absence of an excess of FlAsH (data not shown).

The observed αS oligomer-specific FlAsH fluorescence signals of PG65 (FIG. 1B) was encouraging, and αS oligomerization was monitored during αS aggregation using FlAsH fluorescence of PG65. αS aggregation was initiated by incubation of freshly prepared αS solution at 350 μM and 37° C. with constant shaking. Aliquots of αS samples were withdrawn at several time points during incubation, mixed with Thioflavin T (i.e., a fluorescent dye specific for cross β sheet structures present in amyloid fibrils[20], ThT) or FlAsH and freshly-prepared PG65, and aggregation states of the samples were then examined using ThT fluorescence and FlAsH fluorescence of PG65 (FIG. 2). Time-course ThT fluorescence exhibited a sigmoidal increase, in agreement with previous studies on αS aggregation.[7b] Importantly, maximal RFCs occurred at ~6 h-1 day (FIG. 2), a period in close agreement with previous reports for maximal concentration of transient αS oligomeric species formed during incubation under similar conditions.[12] The significant increase in RFC prior to the onset of a ThT fluorescence increase followed by reduction of RFC upon further incubation (FIG. 2) is in agreement with the previous findings on certain αS oligomers occurring as transient intermediate species on the fibrillation pathway.[7b,12,21] The presence of αS oligomers and αS fibrils after 1 and 7 day incubations, respectively, was confirmed by TEM (FIG. 2). Taken together, the instant results suggest that PG65 detected the formation of transient αS oligomers. In addition, PG65 generated different levels of FlAsH fluorescence signals with structurally similar yet distinct amyloid oligomers (see the supporting text and FIGS. 7 and 8).

αS-PG65 binding was then examined using native PAGE and fluorescent dot blot assays, and their relevance to FlAsH fluorescence signalling. The instant results suggest that PG65 was bound to HMW αS oligomers, which represented the major population in the αS oligomer samples, and this binding was responsible for generation of FlAsH fluorescence signals (FIG. 9). In contrast, no significant binding between PG65 and αS monomers was present (FIGS. 9A and 3B) presumably due to a relatively high thermodynamic cost of assembly between these two structurally disordered entities. Interestingly, PG65 was bound to LMW αS oligomers, which were present as the small fraction in αS monomer samples (FIGS. 9A and 6A) as well as αS fibrils with no weaker affinity than to αS HMW oligomers (FIG. 9). Collectively, the binding results suggest that generation of PG65 fluorescence signals did not simply depend on binding events, but also on aggregation states of αS.

Figure 10:
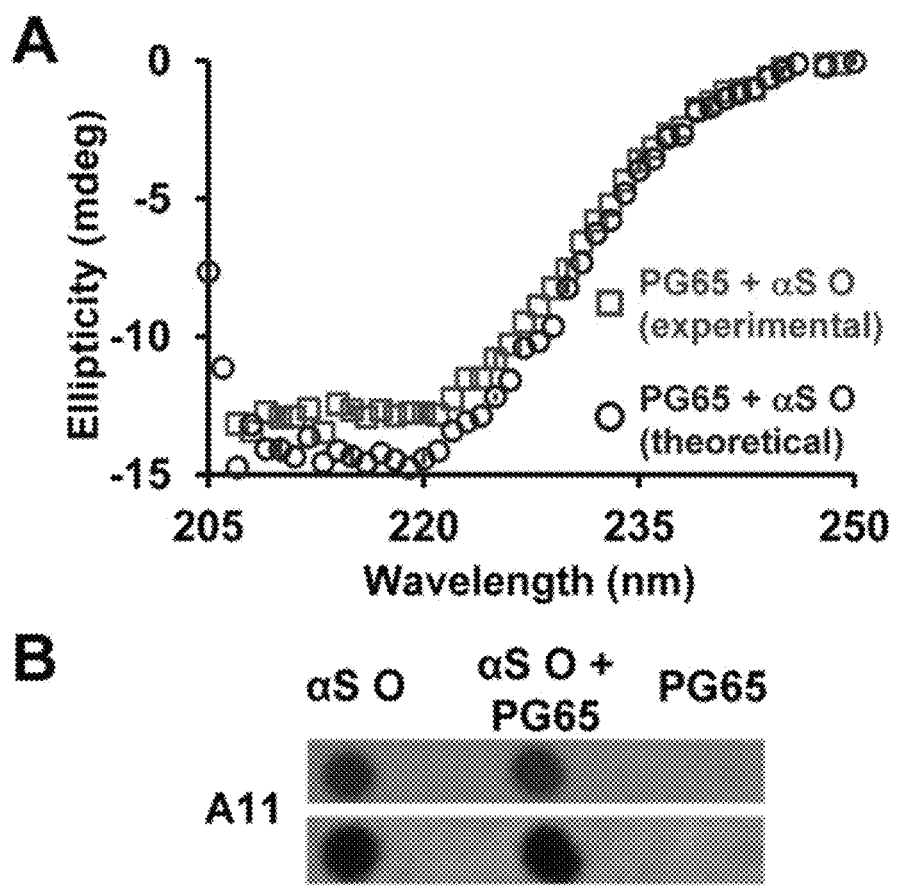
FIG. 10A shows a CD spectrum of a mixture of PG65+αS oligomer sample shown along with their corresponding theoretical mixture (i.e., the simple sum of the individual spectra for PG65 only and αS oligomer sample only under the otherwise same conditions). Concentration of PG65: 2.6 μM and concentration of αS: 13 μM. Error bars (i.e., 1 SD are included at every 5 nm and smaller than data symbols. PG65 at <2.6 μM was not used because of low signal-to-noise ratios of CD signals under this condition. No significant difference in CD spectra of protein samples was detected in the presence and absence of an excess of FlAsH (see above) (data not shown).
FIG. 10B shows dot blot assays of αS oligomer samples (O) with and without PG65 using a conformation-specific antibody, A11. [αS O]/[PG65]=1:1 (top) and 5:1 (bottom).
Figure 11:
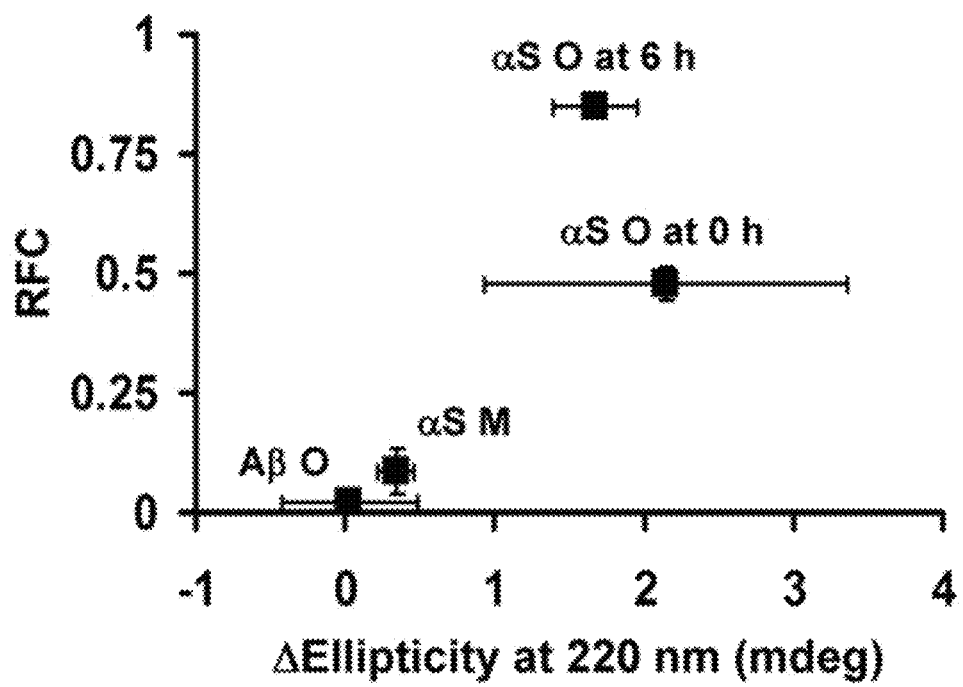
FIG. 11 shows relative FlAsH fluorescence change (RFC) compared against the ellipticity difference at 220 nm between actual and theoretical mixtures of PG65 at 2.6 μM with αS monomers (αS M), αS oligomers prepared after 0 h incubation (αS O at 0 h), αS oligomers prepared after 6 h incubation (αS O at 6 h) and Aβ oligomer samples (Aβ O) each at 13 μM. This plot suggests that secondary structure change of PG65 was necessary to yield significant RFC. The errors were evaluated using the propagation of error method.

It was then investigated whether binding to different αS species could result in signalling to such a varying extent through conformational changes of PG65. For this examination, a CD spectrum of a mixture of PG65 and αS oligomers (i.e., mostly HMW) was compared with a simple sum of CD spectra for individual samples under the otherwise same condition (FIG. 10A). Importantly, this comparison indicates the presence of significant conformational changes upon mixing of PG65 and αS HMW oligomers. The following findings support that major structural changes occurred in PG65 rather than αS HMW oligomers upon binding to each other: 1) binding to αS HMW oligomers altered the aggregation states of PG65 from homo-monomeric to hetero-oligomeric (FIG. 9B); 2) oligomeric states of αS HMW oligomers remained unaffected upon binding to PG65 (FIG. 9B); 3) A11-positive conformations of αS HMW oligomers remained unchanged in the presence of A11-negative PG65 (FIG. 10B). Importantly, little or no significant conformational changes of PG65 occurred with αS monomer samples (FIG. 11) despite strong binding of PG65 to αS LMW oligomers present in these αS samples (FIGS. 9A and 9C). Interestingly, these features of PG65 resemble other naturally existing IDPs adopting different bound conformations according to the structural templates provided by binding partners.[16] The αS HMW oligomer-dependent structural changes of PG65 may be related to the intrinsic nature of αS-derived sequences contained in PG65 and/or its CCPGCC motif (SEQ ID NO: 1). Pro-Gly displays a strong preference in the i−1 and i+2 positions of type-I' and -II β-turns[22], which may be compatible with specific β sheet arrangements found in αS oligomers.[7b] The CD analyses were extended to mixtures of PG65 and other oligomers, and it was found that significant ellipticity changes were necessary for relatively large RFC values (FIG. 11), consistent with the notion that FlAsH fluorescence signaling of PG65 was mediated by its conformational changes. Nature often relies on molecular switching where biomolecules undergo ligand binding-induced conformational changes for rapid and specific signalling.[23] High structural flexibility of IDPs such as αS[1] makes them highly capable of evolving into rapid-responsive, conformation-switching probes, as evident in the present study. Recent identification of more IDPs should expand a repertoire of molecular scaffolds for such probes.[20]

Materials and Methods

Reagents

Oligonucleotides were purchased from Operon Biotechnologies Inc. (Huntsville, Ala., USA). High-fidelity Platinum Pfx DNA polymerase and Electromax DH5α-E cells were purchased from Life Technologies (Grand Island, N.Y., USA). All DNA purification kits were purchased from Qiagen (Valencia, Calif., USA). FPLC columns for purification were purchased from GE Healthcare (Rahweh, N.J., USA). Restriction enzymes and T4 DNA ligase were purchased from New England Biolabs (Ipswich, Mass., USA). Antibiotics and biological reagents were purchased from Thermo Fisher Scientific (Suwanee, Ga., USA). Antibodies recognizing the N and C-terminus of S were purchased from Santa Cruz Biotechnologies (Santa Cruz, Calif., USA). A conformation-specific antibody, A11, was purchased from Life Technologies (Grand Island, N.Y., USA).

DNA Construction

The plasmid pRK172[24] was used for expression of αS, PG65, PG65F, PG83 and PG83F. DNA sequences coding for protein probes were created by overlap extension PCR. The desired PCR products were purified by QIAquick PCR purification and QIAquick gel-extraction kits. The purified DNA sequences were digested by NdeI and HindII restriction enzymes to create the sticky ends needed for ligation. Plasmid pRK172 was digested with the same enzymes, and purified with a QIAquick gel-extraction kit. The digested inserts and plasmids were then ligated using T4 ligase. Ligation products were then electroporated into Electromax DH5α-E (90 µL) by using a Bio-Rad Gene Pulser (Hercules, Calif., USA). Electroporated cells were subsequently incubated for 1 h at 250 rpm and 37° C. in a New Brunswick Scientific Innova TM4230 incubator (Edison, N.J., USA). Electroporated cells were then plated on an LB agar plate supplemented with ampicillin (100 µg mL$^{-1}$) and incubated for 16-24 h at 37° C. in the incubator. The colonies growing on the ampicillin-supplemented LB agar plate were picked and re-cultured in test tubes containing LB medium (10 mL) and ampicillin (100 µg mL$^{-1}$). Plasmid DNA was extracted from re-cultured colonies by using a QIAprep spin miniprep kit according to the manufacturer's protocol. The extracted DNA was then sequenced at Genewiz, Inc. (South Plainfield, N.J., USA). Cysteine to serine mutations were introduced into a gene encoding PG65 by Quikchange mutagenesis (Agilent Technologies, Santa Clara, Calif., USA) and confirmed by DNA sequencing.

Protein Expression and Purification

LB medium (1 L) containing ampicillin (50 µg mL$^{-1}$) was inoculated with 1% overnight culture and shaken at 250 rpm and 37° C. Cells expressing αS and protein probes were grown at 37° C. until the OD$_{600}$ reached 1.0. Expression of αS and protein probes was then induced by adding isopropyl-β-D-1-galactopyranoside (IPTG, 1 mM). After induction, the cell culture was shaken for another 18-20 h at 250 rpm and 25° C. to express the proteins. Cells were pelleted by centrifugation at 4400 g and 4° C. for 20 min in a Beckman Coulter Avanti JE centrifuge (Fullerton, Calif., USA). The pelleted cells were then stored at −80° C. until use.

For protein purification, the pelleted cells were resuspended in Tris.HCl buffer (50 mM, pH 8.0) at a dilution ratio of approximately 10 mL per gram of cells. The cells were then lysed by sonication using a Branson Sonifier 150 (Danbury, Conn., USA), and the cell lysates were centrifuged at 39000 g and 4° C. for 1 h. Supernatants containing soluble proteins were then recovered and heat-treated at 80° C., followed by another centrifugation at 39000 g and 4° C. Heat-treated supernatant was then passed through an anion-exchange column (HiTrap Q XL, GE Healthcare) where bound proteins (i.e., αS and probes) were eluted with NaCl (0.35 mM). Fractions containing proteins were then concentrated approximately ten-fold and run through a SEC column (HiPrep 16/60 Sephacryl S-100 High Resolution, GE Healthcare). Following SEC, proteins were desalted on a HiPrep 26/10 Desalting column (GE Healthcare), and eluted in deionized $H_2O$. Purified proteins were then lyophilized, and their identities were confirmed by MALDI-TOF mass spectrometry and dot blot assays using antibodies that recognize the N- or C-terminus of αS. The purities of the proteins were estimated by SDS-PAGE with Coomassie Blue staining to be greater than 95% (data not shown). Purification of protein probes followed a similar process, all in the presence of 1 mM TCEP. After SEC, protein probe solutions were aliquoted and stored at −80° C. until use.

αS Sample Preparation

For preparation of αS monomer samples, lyophilized αS was solubilized at a concentration of ~350 μM in phosphate buffered saline with azide (PBSA, 20 mM $Na_2HPO_4$/$NaH_2PO_4$, 150 mM NaCl, 0.02% (w/v) $NaN_3$, pH 7.2). αS samples were then filtered using 100 kDa cutoff Amicon Ultra centrifugal filters (Millipore, Billerica, Mass., USA) with collection of the filtrate. Note that 100 kDa cutoff membranes were used for ultrafiltration to prepare monomeric αS (MW: 14.5 kDa). This is because αS monomers are natively unfolded and thus display the hydrodynamic size corresponding to that of ~60 kDa globular proteins.[1,25] Filtrates were used for subsequent characterizations without any additional separation.

For preparation of αS oligomer samples, lyophilized αS was dissolved at ~420 μM in PBSA. Protein samples were filtered with 0.45 μm syringe filters into glass vials, and the concentrations of the filtered protein solutions were measured using the absorbance at 280 nm in 8 M urea.[26] The concentrations of filtered protein solutions in PBSA were immediately adjusted to 350 μM by the addition of buffers. Protein solutions were then subject to incubation under continuous shaking conditions for 6 h, followed by ultrafiltration through 100 kDa cutoff centrifugal filters with collection of the retentate.

αS fibril samples were prepared similar to the preparation of αS oligomer samples, except for prolonged incubation of αS solution for ~2-3 weeks followed by centrifugation, multiple washing and rinsing with PBSA, and resuspension of the insoluble fraction in PBSA.

Concentrations of αS herein are monomer-equivalent molar concentrations, unless otherwise mentioned.

B Amyloid (Aβ) Sample Preparation

Samples of Aβ containing 42 amino acids were prepared as described in our previous study[27] (Hu, Y., et al., A peptide probe for detection of various beta-amyloid oligomers, Molecular bioSystems 2012, 8 (10), 2741-52) where Aβ lyophilized powders were pre-treated with hexafluoroisopropanol (HFIP) and then re-lyophilized.

For preparation of Aβ monomer samples, the HFIP-treated, re-lyophilized Aβ was solubilized at 400 μM with 10 mM NaOH for 10 min. Aβ solution in NaOH was then diluted ~10-fold into PBSA (50 mM $Na_2HPO_4$/$NaH_2PO_4$, 150 mM NaCl, 0.02% (w/v) $NaN_3$, pH 7.4). Aβ monomer samples were freshly prepared and used immediately. These Aβ monomer samples displayed largely irregular structures as determined by CD spectroscopy, a lack of large aggregates as confirmed by transmission electron microscopy (TEM), and no significant fluorescence when mixed with Thioflavin T (ThT).

For preparation of Aβ oligomer samples, solutions containing Aβ monomers described above were incubated at 55 μM and room temperature without any shaking. After ~3-4 days of incubation, Aβ soluble oligomers were separated from precipitates by centrifugation. These Aβ oligomer samples contained protofibrils and displayed β sheet structures. In these Aβ oligomer samples, ~70% of Aβ molecules existed at oligomeric states with the remainder at monomeric states, as determined by SEC. These Aβ oligomer samples displayed ThT fluorescence, ~35% of those intensities displayed by Aβ fibrils.

For preparation of Aβ fibrils, the HFIP-treated, re-lyophilized Aβ was dissolved in 50% HFIP in water at 25 μM, followed by evaporation of HFIP by applying a gentle stream of $N_2$ for 2 days with agitation. Aβ samples were then incubated for ~4-6 weeks at room temperature with continuous stirring, followed by centrifugation and resuspension of insoluble fibril fractions with PBSA. These Aβ fibril samples displayed high ThT fluorescence and mature fibrillar morphology.

Measurement of FlAsH Fluorescence of PG65

Fresh aliquots of PG65 solutions at 50 μM in PBSA containing 1 mM tris(2-carboxyethyl)phosphine (TCEP) was diluted 100-fold at room temperature into aqueous buffers containing αS and 90 μM TCEP and 100 μM 1,2-ethanedithiol (EDT). The final concentration of PG65 after 100-fold dilution was 0.5 μM. A similar dilution was made into the same buffers containing 90 μM TCEP and 100 μM EDT without αS as a control. As another control, PBSA containing 1 mM TCEP was diluted 100-fold into αS solutions containing 90 μM TCEP and 100 μM EDT. The final concentrations of TCEP and EDT were kept at 100 μM, in all samples (i.e., PG65 only, αS only and a mixture of PG65 plus αS). Similar addition of competing thiols (e.g., TCEP and EDT) strongly favors binding of FlAsH to a continuous tetracysteine motif, such as one contained in PG65, relative to non-continuous multiple cysteines.[18] The samples were incubated for 1 h at room temperature to allow binding between PG65 and αS to a sufficient extent. After the initial 1 h incubation, 200 μM of FlAsH-$EDT_2$ in DMSO was diluted 133-fold into samples of PG65 only, αS only and a mixture of PG65 plus αS. The final concentration of FlAsH was 1.5 μM, unless otherwise mentioned. The samples were then further incubated for an additional 1 h prior to FlAsH fluorescence measurements using a Photon Technology QuantaMaster QM-4 spectrofluorometer. The final volumes of samples in cuvettes for FlAsH fluorescence measurements were 150 μl. The excitation wavelength was 508 nm and emission was monitored at 536 nm. The data obtained were used for calculation of relative FlAsH fluorescence changes (RFFCs) as signals, i.e., the absolute value ratio of (FlAsH fluorescence emission intensity of a mixture of PG65 plus αS—(FlAsH fluorescence emission intensity of PG65 only+FlAsH fluorescence emission intensity of αS only))/(FlAsH fluorescence emission intensity of PG65 only). As such, this ratio must be 0 when there is no FlAsH fluorescence change of PG65 in the presence of αS. The errors were evaluated by the propagation of error method using data obtained from measurements of at least six samples (i.e., ≥2 samples for PG65 only, ≥2 samples for αS only and 2 samples for a mixture of PG65 plus αS). Concentrations of PG65 and αS are monomer-equivalent molar concentrations. All samples were prepared in siliconized tubes. No significant difference in RFFC was observed when samples were incubated for 30 min in each step (1 h total). During incubation with PG65, aggregation states of αS (e.g., oligomeric) remained unchanged (FIGS. 2A and 2B). PG65 at <0.5 µM was not used herein because of the relatively low signal-to-background ratio of FlAsH fluorescence. Concentrations of αS tested were 0-5 µM. Higher concentrations of αS were not tested due to the non-negligible background FlAsH fluorescence from αS under this condition, particularly at the oligomeric and fibrillar states, presumably due to non-specific binding of FlAsH to solvent-exposed hydrophobic domains of αS oligomers and αS fibrils. RFFCs of other protein probes (i.e., PG65F, PG83 and PG83F) with αS were measured similarly.

Detection of αS using FlAsH fluorescence of PG65 at 0.5 µM was carried out with 1.5 µM of FlAsH for maximal FlAsH fluorescence based on the following observations: when FlAsH fluorescence of PG65 at 0.5 µM was measured with increasing concentrations of FlAsH, RFFC values did not alter significantly with concentrations of FlAsH higher than 1.5 µM in the presence and absence of αS monomers, oligomers, or fibrils (data not shown), indicating that FlAsH is in excess under this condition.

Fluorescent Labeling of αS and PG65

Purified PG65 and αS were labeled with highly photostable Alexa Fluor 647 and Alexa Fluor 488 (Life Technologies), respectively. Succinimidyl-ester forms of these dyes were mixed with purified proteins at pH 7.2 to promote N-terminal (α-amine) labeling according to the manufacturer's protocol. For this labeling, the ratio of fluorescent dye to protein concentrations was adjusted to achieve a final labeling molar ratio of ~1:3-4. Alexa Fluor 488-labeled αS was separated and collected from SEC on a HiPrep 16/60 Sephacryl S-100 column, desalted using a HiPrep 26/10 desalting column, then lyophilized and stored at −80° C. until use. Alexa Fluor 647-labeled PG65 was aliquoted after SEC in PBSA containing 1 mM TCEP and stored at −80° C. until use. A labeled protein was mixed with the corresponding unlabeled protein at a molar ratio of 1:100 for sample preparation. Note that similar N-terminal labeling did not affect self-assembly properties of αS and αS linker mutants.[6]

Time-Course αS Aggregation

αS samples used for time-course aggregation analyses were prepared in a similar manner as outlined above in αS sample preparation where incubation was necessary (i.e. oligomers and fibrils). Proteins in solution at the beginning of incubation were found to be mostly monomeric, as determined by SEC[6]. These samples were incubated at 37° C. with constant shaking at 250 rpm in a New Brunswick Scientific Innova TM4230 incubator to initiate aggregation. Aliquots were removed at different time points during the aggregation process for measurements of RFFC and ThT fluorescence as well as TEM imaging. Samples were also blotted onto a nitrocellulose membrane for A11 dot blot assays.

8-anilino-1-naphthalenesulfonic acid (ANS) fluorescence

αS solutions at a final concentration of 1.6 µM were mixed with a solution of ANS at 16 µM in PBSA. The ANS fluorescence of the samples was then immediately measured with an excitation wavelength of 350 nm, and emission was monitored at 475 nm.

Circular Dichroism (CD) Spectroscopy

Secondary structures of proteins in solution were determined by using CD. Spectra were collected on a Jasco J-815 spectropolarimeter in the far-UV range with a 0.1 cm pathlength cuvette. The spectrum of the background (buffer only) was subtracted from the sample spectrum.

Thioflavin T (ThT) Fluorescence

αS solutions (1.2 µL) were mixed with a solution of ThT (1 µL, 1.0 mM in water) and PBSA (197.8 mL). The ThT fluorescence of the samples was then immediately measured on a Photon Technology QuantaMaster QM-4 spectrofluorometer. The excitation wavelength was 440 nm, and emission was monitored at 487 nm.

Dot Blot Assays

Proteins (1 µg) in aqueous buffer were applied to a nitrocellulose membrane and allowed to air dry at room temperature. Blocking, washing, incubation with primary and alkaline phosphatase-conjugated secondary antibodies, and chemiluminescent development were performed according to the manufacturer's protocols. A fluorescent dot blot assay using Alexa Fluor 647-labeled PG65 with cysteine to serine mutations as a probe was performed similarly, with the exception of the secondary antibody incubation. In this case, detection was achieved using the Molecular Dynamics Storm 840 molecular phosphorimager system housed at the NYU Chemistry Department Shared Instrumentation Facilities Center.

Transmission Electron Microscopy (TEM)

The aliquots (5 µL) of a sample were placed on carbon membrane coated, glow discharged grids and negatively stained with 3% uranyl acetate in deionized water for 15 min. The samples were imaged on a Philips CM12 Transmission Electron Microscope (FEI Corp. Hillsboro, Oreg., USA) at 120 kV with a 4 k×2.67 k GATAN digital camera located at the Image Core Facility of the Skirball Institute of Biomedical Sciences, NYU School of Medicine.

Size Exclusion Chromatography (SEC)

Aggregation states of samples were analyzed with size exclusion chromatography (SEC) using a precision column prepacked with Superdex 200 (GE healthcare) on a GE FPLC system, as described previously.[6] Briefly, the mobile phase flow rate was set at 0.1 ml/min and elution peaks were detected by UV absorbance at 280 nm. The mobile phase buffer was PBSA used for preparation of αS and protein probe samples. As reported previously[1,28], αS monomers (MW: 14.5 kDa) eluted from Superdex 200 with the elution time corresponding to an apparent molecular weight of 60 kDa globular proteins. This is due to the effect of the natively unfolded conformation of αS monomers on their Stokes radius as described previously.[1,28]

In-Gel Fluorescence Imaging

In-gel fluorescence imaging of native PAGE gels was carried out using the Storm 840 molecular phosphorimager system. For in-gel fluorescence imaging, Alexa Fluor 647-labeled PG65 prepared with a labeling ratio of ~0.1 was used directly without any further mixing with unlabeled PG65. Samples containing a mixture of Alexa Flour 488-labeled αS at a designated concentration+Alexa Fluor 647-labeled PG65 at 3.4 µM or Alexa Flour 488-labeled αS only samples were prepared and incubated for 1 h prior to running native-PAGE.

Characterization of αS Samples: Monomeric, Oligomeric and Fibrillar Species Prepared In Vitro Molecular and morphological properties of αS aggregate species that were prepared in vitro were characterized and compared with results from similar previous characterization. Overall, our αS monomer, αS oligomer and αS fibril samples exhibited distinct molecular and morphological properties, which were in agreement with those previously reported elsewhere.[3,4]

αS monomer samples prepared using the instant method displayed no significant fluorescence when mixed with thioflavin T (ThT, FIG. 6C), a fluorescent dye specific for cross β sheet structures present in amyloid fibrils.[5] No immuno-specific signal was detected when these αS monomer samples were probed with A11 (FIG. 6D), an antibody known to recognize certain conformations of amyloid oligomers, including αS oligomers.[3,6] Solvent-exposed hydrophobicity of αS in these samples was low as determined by fluorescence of 1-anilinonaphthalene-8-sulfonic acid (ANS) (FIG. 6E), a fluorescent marker for exposed hydrophobic patches.[7] In these αS samples, structurally disordered monomeric αS represented the dominant fraction as determined by native PAGE and CD analyses (FIGS. 6A and 6B), while the presence of low molecular weight (LMW) oligomeric αS was also detected in a native PAGE gel (FIG. 6A) and TEM images (FIG. 6F), as described previously.[3,4] Additional separation of LMW αS oligomers from αS monomer samples was not performed.

The instant αS oligomer samples contained αS species referred to herein as high molecular weight (HMW) oligomeric αS, which migrated more slowly than LMW αS oligomers and αS monomers in native PAGE (FIG. 6A) and were mostly β sheet-structured (FIG. 6B). Similar electrophoretic patterns of αS monomers, and LMW and HMW αS oligomers were reported in a previous native PAGE analysis.[3,4] No significant ThT fluorescence was observed with the instant αS oligomer samples, indicating the lack of αS fibrillar structures in these samples (FIG. 6C). These αS oligomer samples were significantly ANS-fluorescent (FIG. 6E) and A11-positive (FIG. 6D), indicating the existence of solvent-exposed hydrophobic patches and specific amyloid oligomer conformations, consistent with previous findings.[3,4] The predominant presence of prefibrillar and "donut-like" annular oligomers (FIG. 6F, inset) was detected in these αS oligomer samples by TEM. αS oligomers with similar molecular and morphological characteristics were previously shown to be cytotoxic[3,8,9], indicating the biological relevance of our αS oligomer samples.

αS fibrillar samples prepared herein displayed a much higher ThT fluorescence signal when compared to αS monomers and αS oligomers (FIG. 6C). The instant αS fibril samples exhibited significant ANS fluorescence (FIG. 6E) and were A11-negative (FIG. 6D), as reported similarly elsewhere.[3,4,6,10] TEM images confirmed the presence of mature fibrils in these samples (FIG. 6F).

Different FlAsH Fluorescence Responses of PG65 with Other Amyloid Oligomers

Similarly sized αS oligomers (e.g., αS HMW oligomers) prepared under different incubation conditions (e.g., duration of incubation) may display different structures in terms of β strand arrangements in β sheet structures.[3] It was queried herein whether PG65 generated different FlAsH fluorescence signals with αS oligomers formed after different lengths of incubation time. To this end, αS oligomers (i.e., mostly HMW) were isolated after 0 and 6 h incubation using ultrafiltration for comparative studies. αS oligomers at 0 and 6 h displayed slightly different CD signals and ANS fluorescence (FIGS. 7A and 7B) while other molecular properties characterized by ThT fluorescence, an A11 dot blot assay and TEM (FIGS. 7C and 7E) are relatively similar. When mixed with PG65 and FlAsH, αS oligomers at 0 h exhibited ~2-fold lower RFC compared to those formed after 6 h at the same αS concentration (FIG. 7F), showing that PG65 generated different levels of FlAsH fluorescence signals with similar yet different αS oligomers.

Figure 8:
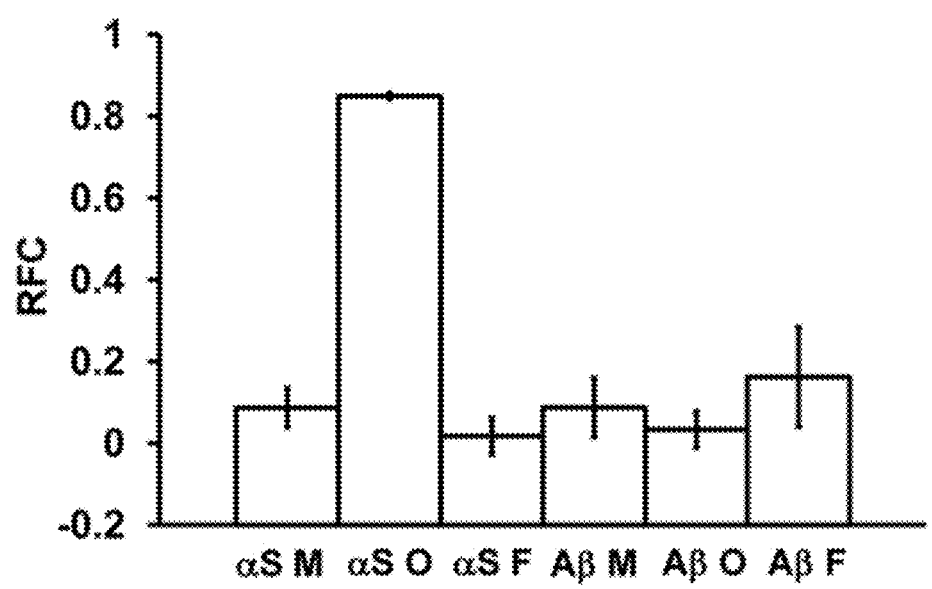
FIG. 8 shows relative FlAsH fluorescence change (RFC) of PG65 at 0.5 µM with αS monomer sample (αS M), αS oligomer sample (αS O), αS fibril sample (αS F), Aβ monomer sample (Aβ M), Aβ oligomer sample (Aβ O) or Aβ fibril sample (Aβ F) each at 2.5 µM. Errors were evaluated using the propagation of error method.

Detection of a different amyloid protein, β-amyloid (Aβ) implicated in Alzheimer's disease (AD), was also examined by FlAsH fluorescence of PG65. For this test, Aβ monomers, Aβ oligomers and Aβ fibrils were prepared as described above. The Aβ oligomers prepared were A11-positive, β sheet-structured, ThT-responsive and protofibrillar, indicating conformational similarity with αS oligomers we prepared at least partially, though not entirely. Interestingly, PG65 generated no significant FlAsH fluorescence signals with any Aβ species including Aβ oligomers (FIG. 8).

Taken altogether, the instant results show that PG65 generated different levels of FlAsH fluorescence signals with structurally similar yet distinct amyloid oligomers.

Binding Between PG65 and αS

Binding between PG65 and αS was examined using native PAGE and its relevance to FlAsH fluorescence signaling. For specific identification of αS and PG65, these were labeled with Alexa Fluor 488 and Alexa Fluor 647 at their respective N-terminus. The location of the major PG65 bands corresponding to the size of PG65 monomers remained unchanged in the presence of αS monomers (FIG. 9A), indicating the lack of significant binding between these two entities, which was further confirmed by relevant SEC analysis (FIG. 3B). The lack of such binding may be due to a high thermodynamic cost of assembly between structurally disordered protein forms and appears to cause no resulting fluorescence signaling (FIG. 1B). Additional minor bands of PG65 also appeared as a result of its binding to LMW αS oligomers present as the small fraction in αS monomer samples (FIGS. 9A and 6A). While similar minor bands of PG65 were also apparent for a mixture of PG65 and αS oligomer samples (FIG. 9B), new overlapping bands also were observed in this mixture, an indication of binding between HMW αS oligomers and PG65 (FIG. 9B). Moreover, comparison between FIG. 1B and FIGS. 9A and 9B suggests that these new overlapping bands represented the molecular binding event, which triggered generation of FlAsH fluorescence signals. PG65 bound to HMW αS oligomers and FlAsH were isolated after removing free PG65 and free FlAsH using ultrafiltration and measured the quantum yield of this complex with assumption that all PG65 molecules were bound to FlAsH. FlAsH bound to PG65 without αS was also prepared as a control after removing unbound FlAsH using ultrafiltration. The quantum yields of FlAsH in these two cases differed by ~9-fold, which was consistent with the observed RFCs of PG65 with αS oligomer samples (FIG. 1B).

Binding of PG65 to αS was further examined by fluorescence dot blot assays where αS monomer, αS oligomer and αS fibril samples were blotted onto nitrocellulose membranes, probed by Alexa Fluor 647-labeled PG65 and then imaged using fluorescence (FIG. 9C). To minimize any complication associated with formation of disulfide bonds between PG65 and blocking proteins in a dot blot assay, all cysteines of Alexa 647-labeled PG65 were mutated to serines. αS oligomer samples at 10 µg displayed positive signals in this format, further confirming the existence of the molecular binding event between PG65 and αS oligomers as characterized by native PAGE (FIG. 9B). Fluorescent dot blot signals were rarely detected with αS oligomer samples at 1 µg (FIG. 9C). αS monomer samples at 1-10 µg were positive in this assay (FIG. 9C). These results, together with those obtained from native PAGE analyses (FIGS. 9A and 9B), support that PG65 was bound to LMW αS oligomers present in the αS monomer samples presumably more strongly than HMW αS oligomers. Similar positive fluorescent dot blot signals were observed with αS fibril samples at 1-10 µg, indicating that PG65 was bound to αS fibrils with no weaker affinity than to αS HMW oligomers (FIG. 9C). Together with FIG. 1B, the instant binding results suggest that generation of PG65 fluorescence signals did not simply depend on binding events, but also on aggregation states of αS.

PG65 provides a detection system for alpha synuclein oligomers that is rapid, quantitative, sensitive and specific. These characteristics are essential for a detection system where the target analytes consist of transient, structurally unstable alpha synuclein oligomers. Alpha synuclein oligomers have been implicated as the toxic species in Parkinson's disease, yet a cure remains elusive because of the lack of a reliable detection system for alpha synuclein oligomerization. Detection of alpha synuclein oligomers is critical going forward for the development of early diagnostics and therapeutics. Following a combinatorial approach where the sensitivity and specificity of PG65 will be further enhanced, a PG65-based detection system may be used for understanding alpha synuclein oligomerization under physiological conditions (≤1 µM), a high-throughput screening system to enable identification of alpha synuclein oligomerization inhibitors and the quantification of alpha synuclein oligomers in biological samples, since a clinical correlation between oligomerization and severity of symptoms is of scientific and diagnostic interest.

Alpha synuclein aggregation has been analyzed through a variety of different methods, all of which are inappropriate for rapid, quantitative, sensitive and specific detection of alpha synuclein oligomers. Size exclusion chromatography has been used and is not sensitive enough for the low concentrations of alpha synuclein oligomers present or dissolution of oligomers occurs because of dilution. NMR and TEM have been used to study structure and morphology, however these techniques are slow and not suited for a high throughput screening system. Fluorescent dyes, such as Thioflavin T and Congo Red, suffer from cross-reactivity due to the similarly structured nature of alpha synuclein aggregates. Antibody detection systems are also inappropriate due to slow detection and multiple washing and rinsing steps that are not favorable for transient alpha synuclein oligomers. In contrast to the present detection systems currently relied on for the detection of alpha synuclein oligomers, PG65 represents the first such system with the potential for rapid, quantitative, sensitive and specific detection.

By considering the above-mentioned importance, the instant invention, consisting of PG65 and design principles, is a novel and important molecular tool for facile in vitro detection of alpha synuclein oligomers. The instant design principle also can be applied for construction of a wide assortment of protein probes, which distinguish between similarly structured aggregates or analytes. Due to such novel yet significant scientific implications, the instant invention should be highly interesting for the commercialization purpose to design protein probes with the capability to rapidly, quantitatively, sensitively and specifically distinguish between similarly structured analytes.

Based on the above, an illustrative embodiment of the probe of the present invention (for example, PG65) comprises a protein (whose full sequence is shown in FIG. 1A) and FlAsH (a commercially available fluorescent dye). The protein portion contains a binding site (that is, CCPGCC (SEQ ID NO: 1)) of FlAsH and causes different FlAsH fluorescent signals depending on aggregation states of bound alpha synuclein species. In particular, PG65 generates FlAsH fluorescence signals when it is bound to alpha synuclein oligomers.

In use, an illustrative PG65 based probe can be used according to the following illustrative steps:

(a) Prepare fresh PG65 solutions at 50 micromolar concentration in PBSA containing 1 mM tris(2-carboxyethyl)phosphine (TCEP).

(b) Mix a portion of the solution prepared in step (a) with alpha synuclein solution in PBSA containing 90 micromolar concentration of TCEP and 100 micromolar concentration of 1,2-ethanedithiol (EDT). In this step, the volume ratio of the solution prepared in step (a) to alpha synuclein solution in PBSA is 1:100. Thus, the final concentration of PG65 in this step is 0.5 micromolar concentration.

(c) Mix a portion of the solution prepared in step (a) with PBSA (that is, no alpha synuclein) containing 90 micromolar concentration of TCEP and 100 micromolar concentration of EDT. In this step, the volume ratio of the solution prepared in step (a) to PBSA is 1:100. The resulting solution (c) is a control of the solution (b).

(d) Prepare fresh PBSA containing 1 mM TCEP.

(e) Mix the solution prepared in step (d) with alpha synuclein solution in PBSA containing 90 micromolar concentration of TCEP and 100 micromolar concentration of EDT. In this step, the volume ratio of the solution prepared in step (d) to alpha synuclein solution in PBSA is 1:100. The resulting solution (e) is another control of the solution (b).

(f) The final concentrations of TCEP and EDT are 100 micromolar concentration, in all samples (that is, PG65 only (=solution (c)), alpha synuclein only (=solution (e)), and a mixture of PG65 plus alpha synuclein (=solution (b)).

(g) Incubate these three samples (that is, PG65 only (=solution (c)), alpha synuclein only (=solution (e)), and a mixture of PG65 plus alpha synuclein (=solution (b)) for 1 hour at room temperature.

(h) Prepare a 200 micromolar concentration of FlAsH-EDT2 in DMSO.

(i) Mix a portion of the fresh solution of FlAsH-EDT2 in DMSO prepared in step (h) with the PG65 only sample (=solution (c)). The volume ratio of the solution (h) to the solution (c) is 1:133. The final concentration of FlAsH is 1.5 micromolar concentration.

(j) Mix a portion of the fresh solution of FlAsH-EDT2 in DMSO prepared in step (h) with the alpha synuclein only sample (=solution (e)). The volume ratio of the solution (h) to the solution (e) is 1:133. The final concentration of FlAsH is 1.5 micromolar concentration.

(k) Mix a portion of the fresh solution of FlAsH-EDT2 in DMSO prepared in step (h) with the mixture of PG65 plus alpha synuclein (=solution (b)). The volume ratio of the solution (h) to the solution (b) is 1:133. The final concentration of FlAsH is 1.5 micromolar concentration.

(l) incubate solutions (i), (j), and (k) for an addition 1 hour.

(m) measure FlAsH fluorescence of solutions (i), (j), and (k).

The results of the measurements taken in step (m) show that PG65 generated different levels of FlAsH fluorescence signals, which can be used to detect structurally similar yet distinct amyloid oligomers, among other things.

In a further embodiment, a kit is provided for performing the methods of the invention. The kit may contain reagents for determining the presence of one or more alpha synuclein proteins. The kit may contain one or more binding agents or isolating agents for isolating a subset or subsets of alpha synuclein proteins of interest; a lysis solution; and reagents for assaying the presence of the alpha synuclein proteins of interest, such as a reagent containing the protein and fluorescent probe. The kit may contain additional materials suitable for performing the methods of the invention, including multiwell stripes, tissue culture medium, and the like.

The foregoing detailed description of the preferred embodiments and the appended figures have been presented only for illustrative and descriptive purposes and are not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

REFERENCES

1. Weinreb, P. H.; Zhen, W.; Poon, A. W.; Conway, K. A.; Lansbury, P. T., Jr., NACP, a protein implicated in Alzheimer's disease and learning, is natively unfolded. Biochemistry 1996, 35 (43), 13709-15.
2. Breydo, L.; Wu, J. W.; Uversky, V. N., Alpha-synuclein misfolding and Parkinson's disease. Biochimica et biophysica acta 2012, 1822 (2), 261-85.
3. Winner, B.; Jappelli, R.; Maji, S. K.; Desplats, P. A.; Boyer, L.; Aigner, S.; Hetzer, C.; Loher, T.; Vilar, M.; Campioni, S.; Tzitzilonis, C.; Soragni, A.; Jessberger, S.; Mira, H.; Consiglio, A.; Pham, E.; Masliah, E.; Gage, F. H.; Riek, R., In vivo demonstration that {alpha}-synuclein oligomers are toxic. Proc Natl Acad Sci USA 2011, 108 (10), 4194-9.
4. Lindgren, M.; Hammarstrom, P., Amyloid oligomers: spectroscopic characterization of amyloidogenic protein states. The FEBS journal 2010, 277 (6), 1380-8.
5. (a) Iwai, A.; Yoshimoto, M.; Masliah, E.; Saitoh, T., Non-A beta component of Alzheimer's disease amyloid (NAC) is amyloidogenic. Biochemistry 1995, 34 (32), 10139-45; (b) Giasson, B. I.; Murray, I. V.; Trojanowski, J. Q.; Lee, V. M., A hydrophobic stretch of 12 amino acid residues in the middle of alpha-synuclein is essential for filament assembly. The Journal of biological chemistry 2001, 276 (4), 2380-6.
6. Hernandez, M.; Golbert, S.; Zhang, L. G.; Kim, J. R., Creation of aggregation-defective alpha-synuclein variants by engineering the sequence connecting beta-strand-forming domains. Chembiochem: a European journal of chemical biology 2011, 12 (17), 2630-9.
7. (a) Cremades, N.; Cohen, S. I.; Deas, E.; Abramov, A. Y.; Chen, A. Y.; Orte, A.; Sandal, M.; Clarke, R. W.; Dunne, P.; Aprile, F. A.; Bertoncini, C. W.; Wood, N. W.; Knowles, T. P.; Dobson, C. M.; Klenerman, D., Direct observation of the interconversion of normal and toxic forms of alpha-synuclein. Cell 2012, 149 (5), 1048-59; (b) Celej, M. S.; Sarroukh, R.; Goormaghtigh, E.; Fidelio, G. D.; Ruysschaert, J. M.; Raussens, V., Toxic prefibrillar alpha-synuclein amyloid oligomers adopt a distinctive antiparallel beta-sheet structure. The Biochemical journal 2012, 443 (3), 719-26.
8. Vilar, M.; Chou, H. T.; Luhrs, T.; Maji, S. K.; Riek-Loher, D.; Verel, R.; Manning, G.; Stahlberg, H.; Riek, R., The fold of alpha-synuclein fibrils. Proceedings of the National Academy of Sciences of the U.S. Pat. No. 2,008,105 (25), 8637-42.
9. (a) Kim, H. Y.; Cho, M. K.; Kumar, A.; Maier, E.; Siebenhaar, C.; Becker, S.; Fernandez, C. O.; Lashuel, H. A.; Benz, R.; Lange, A.; Zweckstetter, M., Structural properties of pore-forming oligomers of alpha-synuclein. Journal of the American Chemical Society 2009, 131 (47), 17482-9; (b) Kayed, R.; Head, E.; Thompson, J. L.; McIntire, T. M.; Milton, S. C.; Cotman, C. W.; Glabe, C. G., Common structure of soluble amyloid oligomers implies common mechanism of pathogenesis. Science 2003, 300 (5618), 486-9.
10. (a) Miller, Y.; Ma, B.; Nussinov, R., Polymorphism in Alzheimer Abeta amyloid organization reflects conformational selection in a rugged energy landscape. Chemical reviews 2010, 110 (8), 4820-38; (b) Sandberg, A.; Luheshi, L. M.; Sollvander, S.; Pereira de Barros, T.; Macao, B.; Knowles, T. P.; Biverstal, H.; Lendel, C.; Ekholm-Petterson, F.; Dubnovitsky, A.; Lannfelt, L.; Dobson, C. M.; Hard, T., Stabilization of neurotoxic Alzheimer amyloid-beta oligomers by protein engineering. Proceedings of the National Academy of Sciences of the U.S. Pat. No. 2,010, 107 (35), 15595-600.
11. Volles, M. J.; Lee, S. J.; Rochet, J. C.; Shtilerman, M. D.; Ding, T. T.; Kessler, J. C.; Lansbury, P. T., Jr., Vesicle permeabilization by protofibrillar alpha-synuclein: implications for the pathogenesis and treatment of Parkinson's disease. Biochemistry 2001, 40 (26), 7812-9.
12. Giehm, L.; Svergun, D. I.; Otzen, D. E.; Vestergaard, B., Low-resolution structure of a vesicle disrupting α-synuclein oligomer that accumulates during fibrillation. Proceedings of the National Academy of Sciences of the U.S. Pat. No. 2,011,108 (8), 3246-51.
13. Shaltiel-Karyo, R.; Davidi, D.; Frenkel-Pinter, M.; Ovadia, M.; Segal, D.; Gazit, E., Differential inhibition of alpha-synuclein oligomeric and fibrillar assembly in parkinson's disease model by cinnamon extract. Biochim Biophys Acta 2012, 1820 (10), 1628-35.
14. Adams, S. R.; Campbell, R. E.; Gross, L. A.; Martin, B. R.; Walkup, G. K.; Yao, Y.; Llopis, J.; Tsien, R. Y., New biarsenical ligands and tetracysteine motifs for protein labeling in vitro and in vivo: synthesis and biological applications. Journal of the American Chemical Society 2002, 124 (21), 6063-76.
15. Kim, H. Y.; Heise, H.; Fernandez, C. O.; Baldus, M.; Zweckstetter, M., Correlation of amyloid fibril beta-structure with the unfolded state of alpha-synuclein. Chembiochem: a European journal of chemical biology 2007, 8 (14), 1671-4.
16. Uversky, V. N.; Dunker, A. K., Understanding protein non-folding. Biochim Biophys Acta 2010, 1804 (6), 1231-64.
17. (a) Ignatova, Z.; Gierasch, L. M., Monitoring protein stability and aggregation in vivo by real-time fluorescent labeling. Proceedings of the National Academy of Sciences of the U.S. Pat. No. 2,004,101 (2), 523-8; (b) Scheck, R. A.; Schepartz, A., Surveying protein structure and function using bis-arsenical small molecules. Acc Chem Res 2011, 44 (9), 654-65.
18. Krishnan, B.; Gierasch, L. M., Cross-strand split tetra-Cys motifs as structure sensors in a beta-sheet protein. Chemistry & biology 2008, 15 (10), 1104-15.
19. Borghi, R.; Marchese, R.; Negro, A.; Marinelli, L.; Forloni, G.; Zaccheo, D.; Abbruzzese, G.; Tabaton, M., Full length alpha-synuclein is present in cerebrospinal fluid from Parkinson's disease and normal subjects. Neurosci Lett 2000, 287 (1), 65-7.
20. LeVine, H., 3rd, Quantification of beta-sheet amyloid fibril structures with thioflavin T. Methods in enzymology 1999, 309, 274-84.
21. (a) Volles, M. J.; Lansbury, P. T., Jr., Zeroing in on the pathogenic form of alpha-synuclein and its mechanism of neurotoxicity in Parkinson's disease. Biochemistry 2003, 42 (26), 7871-8; (b) Conway, K. A.; Lee, S. J.; Rochet, J.

C.; Ding, T. T.; Williamson, R. E.; Lansbury, P. T., Jr., Acceleration of oligomerization, not fibrillization, is a shared property of both alpha-synuclein mutations linked to early-onset Parkinson's disease: implications for pathogenesis and therapy. Proceedings of the National Academy of Sciences of the United States of America 2000, 97 (2), 571-6.
22. Rose, G. D.; Gierasch, L. M.; Smith, J. A., Turns in peptides and proteins. Advances in protein chemistry 1985, 37, 1-109.
23. Vallee-Belisle, A.; Plaxco, K. W., Structure-switching biosensors: inspired by Nature. Curr Opin Struct Biol 2010, 20 (4), 518-26.
24. (a) Tashiro, M.; Kojima, M.; Kihara, H.; Kasai, K.; Kamiyoshihara, T.; Ueda, K.; Shimotakahara, S., Characterization of fibrillation process of alpha-synuclein at the initial stage. Biochemical and biophysical research communications 2008, 369 (3), 910-4; (b) Conway, K. A.; Harper, J. D.; Lansbury, P. T., Accelerated in vitro fibril formation by a mutant alpha-synuclein linked to early-onset Parkinson disease. Nature medicine 1998, 4 (11), 1318-20; (c) Greenbaum, E. A.; Graves, C. L.; Mishizen-Eberz, A. J.; Lupoli, M. A.; Lynch, D. R.; Englander, S. W.; Axelsen, P. H.; Giasson, B. I., The E46K mutation in alpha-synuclein increases amyloid fibril formation. The Journal of biological chemistry 2005, 280 (9), 7800-7.
25. (a) Fauvet, B.; Mbefo, M. K.; Fares, M. B.; Desobry, C.; Michael, S.; Ardah, M. T.; Tsika, E.; Coune, P.; Prudent, M.; Lion, N.; Eliezer, D.; Moore, D. J.; Schneider, B.; Aebischer, P.; El-Agnaf, O. M.; Masliah, E.; Lashuel, H. A., alpha-Synuclein in central nervous system and from erythrocytes, mammalian cells, and Escherichia coli exists predominantly as disordered monomer. The Journal of biological chemistry 2012, 287 (19), 15345-64; (b) Uversky, V. N.; Li, J.; Souillac, P.; Millett, I. S.; Doniach, S.; Jakes, R.; Goedert, M.; Fink, A. L., Biophysical properties of the synucleins and their propensities to fibrillate: inhibition of alpha-synuclein assembly by beta- and gamma-synucleins. J Biol Chem 2002, 277 (14), 11970-8.
26. Wetlaufer, D. B., Ultraviolet Spectra of Proteins and Amino Acids. Adv. Protein Chem. 1962, 17, 303-390.
27. Hu, Y.; Su, B.; Zheng, H.; Kim, J. R., A peptide probe for detection of various beta-amyloid oligomers. Molecular bioSystems 2012, 8 (10), 2741-52.
28. Fredenburg, R. A.; Rospigliosi, C.; Meray, R. K.; Kessler, J. C.; Lashuel, H. A.; Eliezer, D.; Lansbury, P. T., Jr., The impact of the E46K mutation on the properties of alpha-synuclein in its monomeric and oligomeric states. Biochemistry 2007, 46 (24), 7107-18.

What is claimed is:

1. A kit for detecting αS oligomers, the kit comprising a protein comprising the sequence:

```
                                              (SEQ ID NO: 4)
MDVFMKGLSKAKEGWAAAEKTKQGVAEAAGKTKEGVLYVGSKTKEG

WHGVATVAEKTKEQVTCCPGCCAVVTGVTAVAQKTVEGAGSIAAAT

GFVKKDQLGKNEEGAPQEGILEDMPVDPDNEAYEMPSEEGYQDYEP

EA.
```

2. A conformation-switching fluorescent protein probe for detection of alpha synuclein (αS) oligomers, the protein probe comprising an αS variant in the form of PG65 (SEQ ID NO: 4) in combination with a conformation-sensitive fluorescing molecule, wherein the conformational-sensitive fluorescing molecule is fluorescein arsenical hairpin (FlAsH).

3. The protein probe of claim 2, wherein the αS is a high molecular weight αS oligomer having a molecular weight of at least 100 kDa.

4. The protein probe of claim 3, further comprising binding of the PG65 (SEQ ID NO: 4) to the αS so as to generate fluorescence signals, wherein the PG65 (SEQ ID NO: 4) is bound to the αS whereby the probe generates fluorescence signals.

5. The protein probe of claim 4, for use in the detection of αS oligomers implicated in Parkinson's disease.

6. The protein probe of claim 4, further comprising a linkage between the PG65 (SEQ ID NO: 4) and the αS resulting in the generation of the fluorescence signals, which are modulated by binding-induced conformational changes of the protein probe.

7. The protein probe of claim 6, wherein the linkage provides for detection of the high molecular weight αS oligomers within a one hour time period.

8. The protein probe of claim 7, wherein the linkage is regulated depending on αS aggregation states.

9. The protein probe of claim 8, wherein the PG65 (SEQ ID NO: 4) is created by replacement of a first αS linker region with a tetracysteine motif, CCPGCC (SEQ ID NO: 1), as a binding site for the FlAsH.

10. A method for detecting the presence of an alpha-synuclein protein analyte comprising contacting a protein comprising the sequence:

```
                                              (SEQ ID NO: 4)
MDVFMKGLSKAKEGWAAAEKTKQGVAEAAGKTKEGVLYVGSKTKEG

WHGVATVAEKTKEQVTCCPGCCAVVTGVTAVAQKTVEGAGSIAAAT

GFVKKDQLGKNEEGAPQEGILEDMPVDPDNEAYEMPSEEGYQDYEP

EA,
``` with the alpha-synuclein protein analyte and a conformational-sensitive fluorescent molecule, and detecting fluorescence of the resulting combination,
wherein the conformational-sensitive fluorescent molecule is fluorescein arsenical hairpin (FlAsH).

11. The method of claim 10, wherein the method is performed on a multi-well plate.

12. A method for detecting αS oligomers implicated in Parkinson's disease in a patient in need thereof, comprising contacting a protein comprising the sequence:

```
                                              (SEQ ID NO: 4)
MDVFMKGLSKAKEGWAAAEKTKQGVAEAAGKTKEGVLYVGSKTKEG

WHGVATVAEKTKEQVTCCPGCCAVVTGVTAVAQKTVEGAGSIAAAT

GFVKKDQLGKNEEGAPQEGILEDMPVDPDNEAYEMPSEEGYQDYEP

EA,
``` with a conformational-sensitive fluorescent molecule and a patient's extracellular fluid containing proteins, and detecting fluorescence of the resulting combination,
wherein the conformational-sensitive fluorescent molecule is fluorescein arsenical hairpin (FlAsH).

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Cys Pro Gly Cys Cys
1               5

<210> SEQ ID NO 2
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110
```

```
Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Val Gly Gly
1

<210> SEQ ID NO 4
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Cys Cys Pro Gly Cys Cys Ala Val Val Thr Gly Val Thr Ala Val Ala
65                  70                  75                  80

Gln Lys Thr Val Glu Gly Ala Gly Ser Ile Ala Ala Ala Thr Gly Phe
                85                  90                  95

Val Lys Lys Asp Gln Leu Gly Lys Asn Glu Glu Gly Ala Pro Gln Glu
            100                 105                 110

Gly Ile Leu Glu Asp Met Pro Val Asp Pro Asp Asn Glu Ala Tyr Glu
        115                 120                 125

Met Pro Ser Glu Glu Gly Tyr Gln Asp Tyr Glu Pro Glu Ala
    130                 135                 140

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Arg Trp Cys Cys Pro Gly Cys Cys Lys Thr Phe
1               5                   10
```